United States Patent [19]
Lorant et al.

[11] Patent Number: 5,993,832
[45] Date of Patent: Nov. 30, 1999

[54] OIL-IN-WATER EMULSION, A COMPOSITION COMPRISING THIS EMULSION AND USE OF THIS EMULSION IN COSMETICS AND IN HYGIENE

[75] Inventors: Raluca Lorant, Thiais; Nadia Terren; Sophie Favre, both of Chevilly Larue; Jacqueline Griat, Ablon, all of France

[73] Assignee: L'Oreal, Paris, France

[21] Appl. No.: 08/811,844

[22] Filed: Mar. 5, 1997

[30] Foreign Application Priority Data

Mar. 5, 1996 [FR] France ................................. 96 02750

[51] Int. Cl.$^6$ ...................................................... A61K 7/48
[52] U.S. Cl. ........................... 424/401; 424/69; 424/70.1; 514/844; 514/845; 514/846
[58] Field of Search ............................ 424/401, 69, 701; 514/844, 845, 846

[56] References Cited

U.S. PATENT DOCUMENTS

| | | |
|---|---|---|
| 5,091,493 | 2/1992 | O'Lenick, Jr. et al. . |
| 5,093,452 | 3/1992 | O'Lenick, Jr. . |
| 5,149,765 | 9/1992 | O'Lenick, Jr. . |
| 5,280,099 | 1/1994 | Imperante et al. . |
| 5,286,830 | 2/1994 | Imperante et al. . |
| 5,382,381 | 1/1995 | Imperante et al. . |

FOREIGN PATENT DOCUMENTS

A-0627259  12/1994  European Pat. Off. .

*Primary Examiner*—Jyothsna Venkat
*Attorney, Agent, or Firm*—Finnegan, Henderson, Farabow, Garrett & Dunner, L.L.P.

[57] ABSTRACT

An oil-in-water emulsion comprising an aqueous phase, a fatty phase, at least one silicone surfactant comprising at least one anionic group and at least one acidic compound other than the silicone surfactant, and a composition comprising such an emulsion. The invention also relates to the use of a silicone surfactant comprising at least one anionic group for the preparation of a stable emulsion comprising at least one acidic compound other than the silicone surfactant.

32 Claims, No Drawings

OIL-IN-WATER EMULSION, A COMPOSITION COMPRISING THIS EMULSION AND USE OF THIS EMULSION IN COSMETICS AND IN HYGIENE

The invention relates to an oil-in-water emulsion, to a composition comprising this emulsion and to the use of this emulsion, in particular in cosmetic compositions.

In the cosmetics or dermatological field, acidic active compounds, such as hydroxy acids or α- and β-keto acids, are increasingly used for caring for the face and/or the body. In particular, hydroxy acids are used to give the face a luminous and radiant complexion, and thus a good look, and a smooth and younger appearance; they are also used for the non-therapeutic treatment of wrinkles and/or fine lines of the skin and to remove the comedones due to acne.

Unfortunately, these acidic compounds, and more particularly hydroxy acids, exhibit the disadvantage of destabilizing certain substrates.

It is known that emulsions, such as conventional oil-in-water emulsions, which contain common emulsifiers, such as fatty acid soaps and in particular, triethanolamine stearate, are difficult to prepare and have little stability in the presence of acidic compounds. Indeed, many surfactants have little effectiveness or are incompatible with these acidic compounds.

Moreover, common emulsifiers, used in acidic medium, can easily penetrate into the skin and then cause problems of irritation. In addition, these emulsifiers do not make it possible to emulsify all oils and in particular, silicone oils. Now, silicone oils possess certain cosmetic advantages. In particular, they exhibit the advantage of contributing more softness to the compositions during their application on the skin.

To avoid these disadvantages, emulsions of silicone surfactants have been provided. For example, European Patent Application No. EP-A-435,483 describes a water-in-oil emulsion comprising a volatile polydimethylsiloxane, a polyoxyethylenated and/or polyoxypropylenated polydimethylsiloxane silicone surfactant and a 2-hydroxyalkanoic acid. When applied on the skin, however, these water-in-oil emulsions exhibit the disadvantage of depositing a greasy film on the skin and of not easily penetrating the surface of the skin. The cosmetic properties of these emulsions are therefore unsatisfactory. In addition, because the acidic compounds are present in the dispersed aqueous phase of the emulsion, they contact the skin less rapidly; thus their activity on the skin is slower.

Moreover, oil-in-water emulsions prepared with an oxyethylenated polydimethylsiloxane as surfactant are known from French Application No. FR-A-2 676 921. However, these emulsions are not very stable in the presence of acidic compounds such as hydroxy acids.

The aim of the present invention is to overcome these disadvantages. The present invention provides a composition in emulsion form which is stable in the presence of acidic compounds, while having good cosmetic properties.

Applicants have discovered, surprisingly and unexpectedly, that it is possible to achieve this aim by using a specific silicone surfactant.

In the context of the present invention, the expression "stable emulsion" is understood to mean an emulsion which does not separate by settling after storage for two months at 45° C.

A subject of the invention is thus an oil-in-water emulsion comprising an aqueous phase and a fatty phase, which comprises:

(a) a silicone surfactant containing at least one anionic group, and (b) an acidic compound other than the silicone surfactant.

Another subject of the invention relates to a composition, in particular a cosmetic, pharmaceutical or hygienic composition, comprising an emulsion as defined above.

Moreover, it has been found that the emulsion according to the invention is applied and is spread homogeneously, without leaving a greasy feel. The film obtained also exhibits a light texture and remains comfortable to wear throughout the day. The emulsion applied on the skin forms a protective film which limits the penetration of the acidic compounds into the skin. The risks of irritation due to the acidic compounds are thus reduced, while retaining good activity of these compounds on the skin.

In addition, the surfactants used according to the invention make it possible to completely emulsify silicone oils, which can thus improve the cosmetic properties (lubricating, film-forming, protective or water-resistant properties) of the emulsion according to the invention.

Further, it has been found that it is possible to incorporate pigments into the emulsion according to the invention without encountering a problem of agglomeration of such pigments.

The emulsion according to the invention comprises a silicone surfactant comprising at least one anionic group. The silicone surfactant can thus be an anionic surfactant or an amphoteric surfactant.

According to the invention, the anionic group present in the silicone surfactant can be selected from phosphate, sulphate, sulphonate and/or carboxylate groups. Use is preferably made of silicone surfactants comprising at least one phosphate or sulphate group.

Mention may preferably be made, among silicone surfactants containing a phosphate group, of those of formulae (I) to (IV):

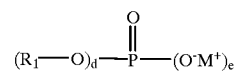

(I)

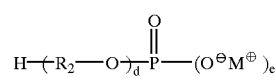

(II)

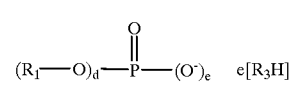

(III)

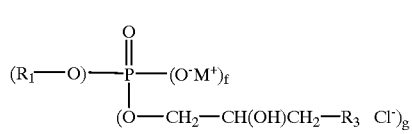

(IV)

wherein:

$R_1$ represents a radical of formula (V):

$$-(C_2H_4O)_z-(C_3H_6O)_y-(C_2H_4O)_x-(CH_2)_3 \qquad (V)$$

$$Me-Si(Me)(Me)-O-[Si(Me)(R_4)-O]_a-[Si(Me)(R_5)-O]_b-[Si(Me)(\text{above})-O]_c-Si(Me)(Me)-Me$$

$R_2$ is a radical of formula (VI):

(VI)

$$-(C_2H_4O)_z-(C_3H_6O)_y-(C_2H_4O)_x-(CH_2)_3-$$

$$Si(CH_3)(CH_3)-O-[Si(CH_3)(R_4)-O]_a-[Si(CH_3)(R_5)-O]_b-[Si(CH_3)(\text{above}) -O]_c-Si(CH_3)(CH_3)-$$

$$-(CH_2)_3-(C_2H_4O)_x-(C_3H_6O)_y-(C_2H_4O)_z-$$

wherein:

$C_2H_4O$ represents a —$CH_2$—$CH_2$—O— group, $C_3H_6O$ represents a —$CH_2$—$CH(CH_3)$—O— group, a is an integer ranging from 0 to 200, b is an integer ranging from 0 to 200, c is an integer ranging from 1 to 200, $R_4$ represents a —$(CH_2)_nCH_3$ or phenyl radical, n being an integer ranging from 0 to 10, and $R_4$ preferably represents a methyl radical, $R_5$ is a —$(CH_2)_3$—$(OCH_2CH_2)_x$—$(OCH_2CH(CH_3))_y$—$(OCH_2CH_2)_z$—OH radical, x, y and z are each integers independently ranging from 0 to 20, and preferably $x+y+z \geq 3$, d and e range from 1 to 2, with d+e=3, f is equal to 0 or 1 and g is equal to 1 or 2, with f+g=2, M is selected from H, Na, K, Li, $NH_4$ and $N(CH_2CH_2OH)_3$, $R_3$ is selected from:

$$-\overset{+}{N}(R_8)(R_7)(R_6)$$

$$R_9-C(O)-N(H)-(CH_2)_{\overline{n}}-\overset{+}{N}(R_{11})(R_{10})-$$

$$R_{12}-\overset{+}{N}\underset{(CH_2-CH_2-O)_{\overline{m}}-(CH_2CH(CH_3)-O)_{\overline{n}}-(CH_2CH_2-O)_{\overline{o}}-H}{(CH_2CH_2-O)_{\overline{m}}-(CH_2CH(CH_3)-O)_{\overline{n}}-(CH_2CH_2-O)_{\overline{o}}-H}$$

and

-continued $$\begin{array}{c} CH_2-N-\\ |\quad\quad\quad\\ CH_2-\overset{+}{C}-R_{13}\\ |\\ N\\ |\\ CH_2CH_2OH \end{array}$$

wherein:

$R_6$ to $R_9$ each independently represent an alkyl radical having from 1 to 20 carbon atoms, $R_{10}$ and $R_{11}$ each independently represent an alkyl radical having from 1 to 3 carbon atoms, $R_{12}$ and $R_{13}$ each independently represent an alkyl radical having from 6 to 20 carbon atoms, m, n and o each independently represent an integer ranging from 0 to 20.

The surfactants of formula (I) are described in particular in U.S. Pat. No. 5,070,171, the disclosure of which is incorporated herein by reference, and are sold under the names PECOSIL PS-100, PECOSIL PS-200 and PECOSIL WDS-100 by the company Phoenix Chemical. The surfactants of formulae (II), (III) and (IV) are in particular described respectively in U.S. Pat. Nos. 5,149,765, 5,093,452 and 5,091,493, the disclosures of which are incorporated herein by reference.

Preferred silicone surfactants containing a phosphate group are those of formula (I).

Mention may preferably be made, among silicone surfactants containing a sulphate group, of those of formula (VII):

(VII)

$$CH_3-Si(CH_3)(CH_3)-O-[Si(CH_3)(R_{14})-O]_{a'}-[Si(CH_3)(R_{15})-O]_{b'}-[Si(CH_3)(R_{16})-O]_{c'}-Si(CH_3)(CH_3)-CH_3$$

wherein $R_{14}$ represents an alkyl radical having from 1 to 8 carbon atoms or a phenyl radical, $R_{15}$ represents a —$(CH_2)_3$—O—$(CH_2CH_2O)_u$—$(CH_2CH(CH_3)$—O$)_v$—$(CH_2CH_2O)_w$—$SO_3^-M^+$ radical, wherein M is selected from Na, K, Li and $NH_4$, $R_{16}$ represents a —$(CH_2)_3$—O—$(CH_2CH_2O)_u$—$(CH_2CH(CH_3)$—O$)_v$—$(CH_2CH_2O)_w$—H radical, in which radicals u, v and w each independently represent an integer ranging from 0 to 100, a' and c' each independently represent an integer ranging from 0 to 50, b' represents an integer ranging from 1 to 50, and preferably c'=0.

The compounds of formula (VII) are in particular described in U.S. Pat. No. 4,960,845, the disclosure of which is incorporated herein by reference.

Among silicone surfactants containing a sulphonate group, mention may preferably be made of those obtained by the reaction of a silicone of formula (VIII):

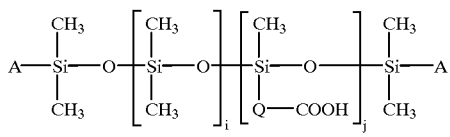

(VIII)

wherein
Q represents $(CH_2)_r$, r being an integer ranging from 3 to 17,
j represents an integer ranging from 1 to 10 and A represents a methyl radical, or j=0 and A represents a —Q—COOH radical,
i represents an integer ranging from 1 to 200, with a taurine derivative of formula $R_{17}$—NH—$(CH_2)_2$—$SO_3M$, wherein
$R_{17}$ represents an alkyl radical having from 1 to 40 carbon atoms, and
M is selected from Na, K, Li and $NH_4$.

These compounds are described in U.S. Pat. No. 5,286,830, the disclosure of which is incorporated herein by reference.

Mention may also be made, as silicone surfactants containing a sulphonate group, of those of formula (IX):

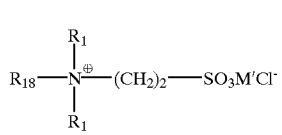

(IX)

wherein
$R_{18}$ represents an alkyl radical having from 1 to 40 carbon atoms,
$R_1$ represents a radical of formula (V) as defined above, and
M' is selected from Na, K, Li and $NH_4$.

The compounds of formula (IX) are in particular described in U.S. Pat. No. 5,280,099, the disclosure of which is incorporated herein by reference.

The silicone surfactant containing an anionic group is preferably present in the emulsion according to the invention in an amount ranging from 0.5% to 15% by weight with respect to the total weight of the emulsion, and more preferably from 2% to 6% by weight.

The emulsion according to the invention also comprises at least one acidic compound other than the silicone surfactant.

In the context of the present invention, the expression "acidic compound" is understood to mean any compound, an aqueous solution or dispersion of which exhibits an acidic pH, i.e., a pH of less than or equal to 7.

The acidic compounds present in the composition of the invention are preferably selected from hydroxy acids and α- and β-keto acids.

The hydroxy acids used in accordance with the present invention are preferably selected from α-hydroxy acids, 5-(n-octanoyl)salicylic acid and salicylic acid.

The α-hydroxy acids to which the invention applies can be linear, branched or cyclic and saturated or unsaturated. The hydrogen atoms of the carbon chain can, in addition, be substituted by halogens or halogenated, alkyl, acyl, acyloxy, alkoxycarbonyl or alkoxy radicals having from 2 to 28 carbon atoms.

The α-hydroxy acids which can be used according to the invention can comprise a mono- or polycarboxylic acid containing one or a number of hydroxyl functional groups, it being necessary for at least one of these hydroxyl functional groups to occupy an α-position on the acid. The α-hydroxy acids of the invention are preferably α-hydroxyalkanoic acids having from 2 to 18 carbon atoms.

Mention may preferably be made, as α-hydroxy acids which can be used in the invention, of glycolic (or α-hydroxyethanoic), lactic (or α-hydroxypropanoic), malic (or hydroxybutanedioic), tartaric (or dihydroxybutanedioic), citric, mandelic, α-hydroxycaprylic (or α-hydroxyoctanoic), α-hydroxyhexanoic, α-hydroxydecanoic, α-hydroxydodecanoic, α-hydroxytetradecanoic, α-hydroxyhexadecanoic, α-hydroxyoctadecanoic, α-hydroxyeicosanoic, α-hydroxydocosanoic, α-hydroxyhexacosanoic and α-hydroxyoctacosanoic acids. Use is more preferably made according to the invention of lactic acid, glycolic acid, citric acid and tartaric acid.

The acidic compounds are preferably present in the emulsions of the invention in amounts ranging from 0.1% to 10% by weight with respect to the total weight of the emulsion, and more preferably from 0.2% to 5% by weight, and even more preferably from 0.5% to 4%.

The emulsions in accordance with the invention preferably have a pH ranging from 2 to 7, and more preferably ranging from 3 to 5.

The fatty phase of the emulsion according to the invention can comprise fatty substances commonly used in the envisaged field of application.

Mention may be made, among the after, of silicone fatty substances, such as silicone oils, pasty fatty substances, gums and waxes, and of non-silicone fatty substances, such as vegetable, mineral, animal and/or synthetic oils, pastes and waxes.

Mention may preferably be made, among silicone fatty substances, of:

(i) poly($C_1$–$C_{20}$)alkylsiloxanes and in particular those containing trimethylsilyl end groups, preferably those with a viscosity of less than 0.06 $m^2$/s, among which may be mentioned polydimethylsiloxanes, which are linear, and alkylmethylpolysiloxanes, such as cetyldimethicone (CTFA name), (ii) volatile silicone oils, such as:
volatile cyclic silicones having from 3 to 8 silicon atoms and preferably from 4 to 5. For example, cyclotetradimethylsiloxane, cyclopentadimethylsiloxane or cyclohexadimethyl-siloxane;
cyclocopolymers of the dimethylsiloxane/methylalkylsiloxane type, such as SILICONE FZ 3109 sold by the company Union Carbide, which is a dimethylsiloxane/methyloctylsiloxane cyclocopolymer; and
volatile linear silicones having from 2 to 9 silicon atoms, for example, hexamethyldisiloxane, hexylheptamethyltrisiloxane or octylheptamethyltrisiloxane;

(iii) phenylated silicone oils, in particular those of formula (X):

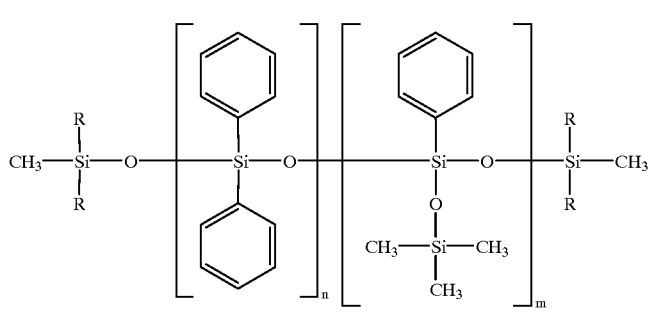

wherein
- R is a $C_1$–$C_{30}$ alkyl radical, an aryl radical or an aralkyl radical,
- n is an integer ranging from 0 to 100,
- m is an integer ranging from 0 to 100, with the proviso that the sum of n and m ranges from 1 to 100; and (iv) silicone gums and silicone waxes.

Mention may preferably be made, among non-silicone fatty substances, of:

(i) volatile hydrocarbon oils, such as isoparaffins and in particular isododecane;

(ii) conventional oils and waxes, such as liquid paraffin, liquid petrolatum, perhydrosqualene, apricot oil, wheat germ oil, sweet almond oil, calophyllum oil, palm oil, castor oil, avocado oil, jojoba oil, olive oil or cereal germ oil; fatty acid esters; alcohols; acetylglycerides; octanoates, decanoates or ricinoleates of alcohols or of polyalcohols; fatty acid triglycerides; glycerides; hydrogenated oils which are solid at 25° C.; lanolins; fatty esters which are solid at 25° C.; beeswax; vegetable waxes, such as carnauba wax, candelilla wax, ouricury wax, Japan wax or cork fibre or sugarcane waxes; mineral waxes, for example paraffin wax, lignite wax or microcrystalline waxes or ozokerits; or synthetic waxes, including polyethylene waxes and the waxes obtained by the Fischer-Tropsch synthesis.

These fatty substances can in particular be selected by the person skilled in the art in order to prepare a composition having the desired properties, for example with respect to consistency or texture. Thus, the fatty phase of the emulsion according to the invention is preferably present in an amount ranging from 2% to 40% by weight with respect to the total weight of the emulsion, and more preferably from 3% to 30% by weight, and still more preferably from 3% to 20% by weight.

In a specific embodiment of the invention, it is possible to prepare an emulsion comprising only silicone fatty substances, in particular volatile cyclic oils, optionally as a mixture with PDMSs and/or phenylated silicone oils.

The aqueous phase of the emulsion according to the invention can comprise water, a floral water, such as cornflower water, or a mineral water, such as VITTEL water, LUCAS water or LA ROCHE-POSAY water. The aqueous phase is preferably present in an amount ranging from 15 to 97.5% by weight with respect to the total weight of the emulsion, and more preferably from 40% to 70% by weight.

The aqueous phase can additionally comprise from 0% to 14% by weight, with respect to the total weight of the aqueous phase, of a lower $C_2$–$C_6$ monoalcohol and/or of a polyol, such as glycerol, butylene glycol, isoprene glycol or propylene glycol.

Moreover, the emulsion according to the invention can comprise from 0 to 5% by weight, with respect to the total weight of the emulsion, of at least one coemulsifier which can be selected from oxyethylenated sorbitan monostearate, fatty alcohols, such as stearyl alcohol or cetyl alcohol, or esters of fatty acids and of polyols, such as glyceryl stearate.

In addition, the emulsion according to the invention can comprise one or a number of thickening agents in preferential concentrations ranging from 0 to 6% by weight with respect to the total weight of the emulsion.

The thickening agent can be selected from:
- polysaccharide biopolymers, such as xanthan gum, locust bean gum, guar gum, alginates, or modified celluloses, such as hydroxyethyl cellulose, methyl cellulose, hydroxypropyl cellulose and carboxymethyl cellulose;
- synthetic polymers, such as polyacrylic acids, such as poly(glyceryl (meth)acrylate) polymers, such as HISPAGEL or LUBRAGEL from the companies Hispano Quimica or Gardian, polyvinylpyrrolidone, poly(vinyl alcohol), crosslinked polymers of acrylamide and of ammonium acrylate, such as PAS 5161 or BOZEPOL C from Hoechst, crosslinked polymers of acrylamide and of 2-acrylamido-2-methylpropanesulphonic acid which is partially or completely neutralized, such as SEPIGEL 305 from Seppic, or crosslinked polymers of acrylamide and of methacryloyloxyethyltrimethylammonium chloride, such as SALCARE SC 92 from Allied Colloids; and
- magnesium aluminium silicate.

The emulsion according to the invention can comprise a particulate phase which can comprise pigments and/or pearlescent agents and/or fillers commonly used in cosmetic compositions.

The pigments can be present in the emulsion in amounts of 0–20% by weight, with respect to the total weight of the emulsion, and preferably in amounts of 2–15%. They can be white or colored, inorganic and/or organic. Mention may preferably be made, among inorganic pigments and nanopigments, of titanium, zirconium or cerium dioxides, as well as of zinc, iron or chromium oxides, nanometre-grade titanium oxides, ferric blue, pearlescent agents, such as mica covered with titanium oxide, with iron oxide, with natural pigment or with bismuth oxychloride, and coloured titanium oxide-coated mica. Mention may preferably be made, among organic pigments, of carbon black and barium, strontium, calcium and aluminium lakes.

The fillers, which can be present in the emulsion in amounts of 0–20% by weight, with respect to the total weight of the emulsion, preferably 2–10%, can be inorganic or synthetic, lamellar or non-lamellar. Mention may preferably be made of talc, mica, silica, kaolin, nylon and polyethylene powders, teflon, starch, titanium oxide-coated mica, natural mother-of-pearl, boron nitride or microspheres, such as EXPANCEL (Nobel Industrie), POLYTRAP (Dow Corning) and silicone resin microbeads (TOSPEARLS from Toshiba, for example).

The emulsion can, in addition, comprise any additive commonly used in the cosmetics field, such as antioxidants, dyes, fragrances, essential oils, preservatives, cosmetic active principles, moisturizers, vitamins, essential fatty acids, sphingolipids, artificial tanning compounds, such as DHA, sunscreening agents, fat-soluble polymers, in particular hydrocarbons, such as polybutene or polyalkylenes, polyacrylates and silicone polymers which are compatible with fatty substances. Of course, the person skilled in the art will take care to choose these possible additional compounds, and/or their amount, so that the advantageous properties of the composition according to the invention are not, or not substantially, detrimentally affected by the envisaged addition.

These additives can be present in the composition in the proportion of 0–10% by weight.

The emulsions according to the invention can constitute all or part of a cosmetic, pharmaceutical or hygienic composition. The compositions can be provided in the form of a colored or non-colored cosmetic product and in particular in the following forms: a care product for the body, face, scalp, and/or the hair, such as a cream, a milk, a gel or a serum; of an anti-sun product; or a make-up product, such as a foundation, a blusher, an eye shadow, an eyeliner, a mascara or a lipstick.

The invention also relates to a process for the non-therapeutic treatment of the skin, scalp and/or hair, characterized in that an emulsion or a composition as defined above is applied on the skin, scalp, and/or hair.

The invention also relates to a process for making up the skin and/or the scalp, characterized in that an emulsion or a composition as defined above is applied on the skin and/or on the scalp.

Another subject of the invention is the use of a silicone surfactant comprising at least one anionic group for the preparation of a stable emulsion comprising at least one acidic compound other than the silicone surfactant.

The invention also relates to the use of a silicone surfactant comprising at least one anionic group for stabilizing an emulsion comprising at least one acidic compound other than the said surfactant.

Examples illustrating the present invention without, however, limiting it will now be given.

EXAMPLES

Examples 1 and 2

Study of the Stability of the Emulsions as Function of the Nature of the Silicone Surfactant An emulsion (care fluid for the face) in accordance with the invention (Example 1) and an oil-in-water emulsion not forming part of the invention (Example 2) were prepared, each emulsion differing in the nature of the silicone surfactant.

The emulsions were prepared according to the following compositions:

| | |
|---|---|
| Apricot kernel oil | 9 g |
| Cyclohexadimethylsiloxane | 9 g |
| Mixture of α-hydroxy acids originating from fruits (29/15/4/1/1 lactic/glycolic/citric/malic/tartaric acids) at 49% in water | 1 g AM |
| Thickening agent | 3 g AM |
| Silicone surfactant | 2.7 g AM |
| Glycerol | 5 g |
| Xanthan gum | 0.3 g |
| Sodium pyrrolidonecarboxylate | 1.5 g |
| Preservatives | q.s. |
| Water | q.s. for 100 g |

The pH of the compositions was 3.5.

The surfactants used for each composition were as follows:

Example 1

Dimethicone copolyol phosphate (CTFA name), sold under the name PECOSIL PS 100 by the company Phoenix

Example 2

Dimethicone copolyol, sold under the name KF 353 by the company Shin Etsu.

Procedure:

These emulsions were prepared in the usual way by first mixing the ingredients of the fatty phase and of the aqueous phase and by then pouring the fatty phase into the aqueous phase with stirring. The polyacrylamide and the acids were then added.

It was found, with a microscope, that the emulsion of Example 1 according to the invention was fine and even and exhibited very good stability. In contrast, the emulsion of Example 2 was coarse and unstable.

Example 3

A care fluid for the face having the following composition was prepared:

| | |
|---|---|
| Apricot kernel oil | 10 g |
| Cyclohexadimethylsiloxane | 10 g |
| Vitamin E | 0:5 g |
| Glycolic acid | 1 g |
| Malic acid | 1 g |
| Silicone surfactant containing a phosphate group (PECOSIL PS 100) | 4 g AM |
| Glycerol | 5 g |
| Xanthan gum | 0.3 g |
| Preservatives | q.s. |
| Sodium hydroxide | q.s. pH 3.5 |
| Water | q.s. for 100 g |

The composition was prepared according to the same procedure as Examples 1–2. The silicone surfactant containing a phosphate group can be replaced by the silicone surfactant containing a sulphate group sold under the name WATER SOLUBLE SULFATE by the company Siltech.

The fluid was provided in the form of an oil-in-water emulsion which was fine and stable. This fluid was easily applied on the face without leaving a feeling of greasiness and provided a slippery feel.

Example 4

A moisturizing body milk having the following composition was prepared:

| | |
|---|---|
| Cyclohexadimethylsiloxane | 15 g |
| Tartaric acid | 1 g |
| Silicone surfactant containing a phosphate group (PECOSIL PS 100) | 5 g AM |
| Glycerol | 3 g |
| Preservatives | q.s. |
| Sodium hydroxide | q.s. pH 4 |
| Water | q.s. for 100 g |

The composition was prepared according to the same procedure as Examples 1–2. A milk was obtained in the form of a stable oil-in-water emulsion. The milk spread easily on the skin and rendered the after soft.

Example 5

A make-up removal milk having the following composition was prepared:

| | |
|---|---|
| Octyl palmitate | 8 g |
| Dioctyl adipate | 5 g |
| Lactic acid | 1 g |
| Silicone surfactant containing a phosphate group (PECOSIL PS 100) | 3.5 g AM |
| Glycerol | 3 g |
| Preservatives | q.s. |
| Triethanolamine | q.s. pH 3 |
| Water | q.s. for 100 g |

The composition was prepared according to the same procedure as Examples 1–2. This make-up removal milk spread very easily on the skin and was very refreshing.

Example 6

A day cream having the following composition was prepared:

| | |
|---|---|
| Octyl methoxycinnamate | 7.5 g |
| Glyceryl stearate | 2 g |
| Cetearyl alcohol | 2 g |
| 2-Octyldodecyl behenate | 9 g |
| Apricot kernel oil | 2 g |
| Citric acid | 1 g |
| Silicone surfactant containing a phosphate group PECOSIL PS 100) | 5 g AM |
| Glycerol | 3 g |
| Preservatives | q.s. |
| Sodium hydroxide | q.s. pH 4 |
| Water | q.s. for 100 g |

The composition was prepared according to the same procedure as Examples 1 and 2, the fatty phase and the aqueous phase being preheated to 70° C. before being mixed.

The cream spread easily on the skin and left a film on the latter which exhibited a light and soft texture.

Example 7

| A foundation having the following composition was prepared: | |
|---|---|
| Cyclohexadimethylsiloxane | 14 g |
| Pigments | 7 g |
| Dispersing agents | 0.2 g |
| Silicone surfactant containing a phosphate group (PECOSIL PS 100) | 5 g |

| A foundation having the following composition was prepared: | |
|---|---|
| Coemulsifier | 2 g |
| Thickening agents | 0.5 g |
| Mixture of α-hydroxy acids originating from fruits (29/15/4/1/1 lactic/glycolic/citric/ malic/tartaric acids) at 49% in water | 1.5 g AM |
| Glycerol | 5 g |
| Preservatives | 0.6 g |
| Sodium hydroxide | q.s. pH 4 |
| Water | q.s. for 100 g |

The composition was prepared in the usual way, by heating the ingredients of the fatty phase, the coemulsifier and the preservatives to 65° C. The aqueous phase was then prepared by mixing the water, the silicone surfactant and the pigments, dispersed beforehand with the dispersing agents, while heating at 80° C. The fatty phase was then poured into the aqueous phase at 65° C. while stirring using a propeller. The thickening agents and the additional preservatives were then added at 40° C. to the emulsion obtained and then the mixture of α-hydroxy acids was added.

It was found that the pigments disperse in this emulsion without forming agglomerates.

The foundation obtained spread easily on the face and was entirely suitable for greasy skins. It behaved well after application.

Example 8

A foundation having the following composition was prepared:

| | |
|---|---|
| Cyclohexadimethylsiloxane | 15 g |
| Pigments | 7 g |
| Dispersing agents | 1 g |
| Silicone surfactant containing a sulphate group (Water Soluble Sulfate) | 5 g AM |
| Coemulsifier | 2 g |
| Thickening agents | 0.5 g |
| Mixture of α-hydroxy acids originating from fruits (29/15/4/1/1 lactic/glycolic/citric/ malic/tartaric acids) at 49% in water | |
| Glycerol | 5 g |
| Preservatives | 0.6 g |
| Sodium hydroxide | q.s. pH 5 |
| Water | q.s. for 100 g |

The composition was prepared according to the same procedure as Example 7.

The foundation obtained spread easily on the skin without a feeling of greasiness and behaved well.

What is claimed is:

1. An oil-in-water emulsion comprising an aqueous phase and a fatty phase, wherein said oil-in-water emulsion comprises:

(a) at least one silicone surfactant containing at least one anionic group; and
   (b) at least one acidic compound other than said at least one silicone surfactant,
   wherein said at least one silicone surfactant is selected from those of formula (I):

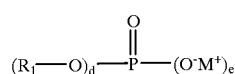

wherein $R_1$ represents a radical of formula (V):

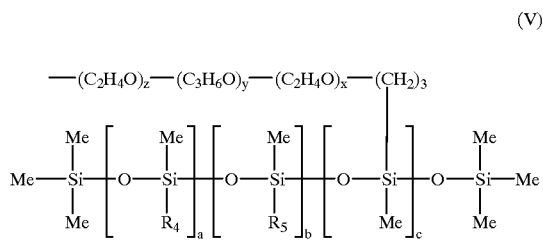

wherein:
Me represents a methyl radical,
$C_2H_4O$ represents a —$CH_2$—$CH_2$—O— group,
$C_3H_6O$ represents a —$CH_2$—$CH(CH_3)$—O— group,
a is an integer ranging from 0 to 200,
b is an integer ranging from 0 to 200,
c is an integer ranging from 1 to 200,
$R_4$ represents a —$(CH_2)_n CH_3$ or phenyl radical, wherein n is an integer ranging from 0 to 10,
$R_5$ represents a —$(CH_2)_3$—$(OCH_2CH_2)_x$—$(OCH_2CH(CH_3))_y$—$(OCH_2CH_2)_z$—OH radical, wherein x, y and z are integers independently ranging from 0 to 20, d and e independently range from 1 to 2, with the provision that d+e=3, and M is selected from H, Na, K, Li, $NH_4$ and $N(CH_2CH_2OH)_3$.

2. An oil-in-water emulsion according to claim 1, wherein said at least one anionic group is a phosphate, a sulphate, a sulphonate or a carboxylate group.

3. An oil-in-water emulsion according to claim 1, wherein said at least one silicone surfactant is present in an amount ranging from 0.5% to 15% by weight with respect to the total weight of the emulsion.

4. An oil-in-water emulsion according to claim 3, wherein said at least one silicone surfactant is present in an amount ranging from 2% to 6% by weight with respect to the total weight of the emulsion.

5. An oil-in-water emulsion according to claim 1, wherein said at least one acidic compound is a hydroxy acid or an α- or β-keto acid.

6. An oil-in-water emulsion according to claim 5, wherein said hydroxy acid is a α-hydroxy acid, 5-(n-octanoyl) salicylic acid or salicylic acid.

7. An oil-in-water emulsion according to claim 6, wherein said α-hydroxy acid is an α-hydroxyalkanoic acid having from 2 to 18 carbon atoms.

8. An oil-in-water emulsion according to claim 6, wherein said α-hydroxy acid is a glycolic, lactic, malic, tartaric, citric, mandelic, α-hydroxycaprylic, α-hydroxyhexanoic, α-hydroxydecanoic, α-hydroxydodecanoic, α-hydroxytetradecanoic, α-hydroxyhexadecanoic, α-hydroxyoctadecanoic, α-hydroxyeicosanoic, α-hydroxydocosanoic, α-hydroxyhexacosanoic or α-hydroxyoctacosanoic acid.

9. An oil-in-water emulsion according to claim 1, wherein said at least one acidic compound is present in an amount ranging from 0.1% to 10% by weight with respect to the total weight of the emulsion.

10. An oil-in-water emulsion according to claim 9, wherein said at least one acidic compound is present in an amount ranging from 0.2% to 5% by weight with respect to the total weight of the emulsion.

11. An oil-in-water emulsion according to claim 1, wherein the pH of said emulsion ranges from 2 to 7.

12. An oil-in-water emulsion according to claim 11, wherein said pH ranges from 3 to 5.

13. An oil-in-water emulsion according to claim 1, wherein said fatty phase comprises fatty substances, wherein said fatty substances are nonvolatile or volatile silicone oils; silicone pasty fatty substances; silicone gums; silicone waxes; nonvolatile or volatile vegetable, mineral, animal or synthetic oils; pastes or waxes, or mixtures thereof.

14. An oil-in-water emulsion according to claim 1, wherein said aqueous phase comprises from 0 to 14% by weight, with respect to the total weight of the aqueous phase, of a lower $C_2$–$C_6$ alcohol and/or a polyol.

15. An oil-in-water emulsion according to claim 1, comprising from 0 to 5% by weight, with respect to the total weight of the emulsion, of at least one emulsifier.

16. An oil-in-water emulsion according to claim 1, comprising from 0 to 6% by weight, with respect to the total weight of the emulsion, of at least one thickening agent.

17. An oil-in-water emulsion according to claim 1, further comprising a particulate phase which comprises from 0 to 20% by weight, with respect to the total weight of the emulsion, of at least one pigment, at least one filler or mixtures thereof.

18. An oil-in-water emulsion according to claim 17, wherein said at least one pigment is present in an amount ranging from 2% to 15% by weight with respect to the total weight of the emulsion.

19. An oil-in-water emulsion according to claim 17, wherein said at least one filler is present in an amount ranging from 2% to 10% by weight with respect to the total weight of the emulsion.

20. A cosmetic, pharmaceutical or hygienic composition, comprising an effective amount of an oil-in-water emulsion according to claim 1.

21. A care product for the body, face, scalp or hair comprising an effective amount of a composition according to claim 20.

22. A care product according to claim 21, which is in the form of a cream, a milk, a gel or a serum.

23. An anti-sun product comprising an effective amount of a composition according to claim 20.

24. A foundation, blusher, eye shadow, eyeliner, mascara or lipstick composition comprising an effective amount of a composition according to claim 20.

25. A process for the non-therapeutic treatment of the skin, scalp, or hair, comprising the step of applying to said skin, scalp or hair an effective amount of an oil-in-water emulsion according to claim 1.

26. A process for making up the skin or scalp, comprising the step of applying to said skin or scalp an effective amount of an oil-in-water emulsion according claim 1.

27. A process for preparing a stable emulsion, said process comprising the steps of combining an effective amount of at least one silicone surfactant containing at least one anionic group with at least one acidic compound other than said at least one silicone surfactant, and emulsifying said combination, wherein said at least one silicone surfactant is selected from those of formula (I):

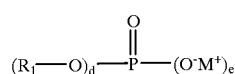
(I)

wherein $R_1$ represents a radical of formula (V):

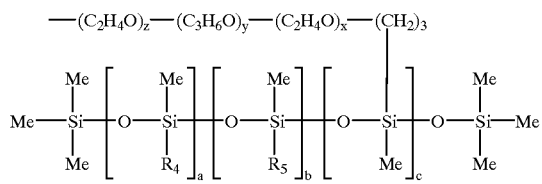
(V)

wherein:
Me represents a methyl radical,
$C_2H_4O$ represents a —$CH_2$—$CH_2$—O— group,
$C_3H_6O$ represents a —$CH_2$—$CH(CH_3)$—O— group,
a is an integer ranging from 0 to 200,
b is an integer ranging from 0 to 200,
c is an integer ranging from 1 to 200,
$R_4$ represents a —$(CH_2)_n CH_3$ or phenyl radical, wherein n is an integer ranging from 0 to 10, $R_5$ represents a —$(CH_2)_3$—$(OCH_2CH_2)_x$—$(OCH_2CH(CH_3))_y$—$(OCH_2CH_2)_z$—OH radical, wherein x, y and z are integers independently ranging from 0 to 20, d and e independently range from 1 to 2, with the provision that d+e=3, and M is selected from H, Na, K, Li, $NH_4$ and $N(CH_2CH_2OH)_3$.

28. An oil-in-water emulsion according to claim 1, wherein said fatty phase is present in an amount ranging from 2% to 40% by weight with respect to the total weight of the emulsion.

29. An oil-in-water emulsion according to claim 28, wherein said fatty phase is present in an amount ranging from 3% to 30% by weight with respect to the total weight of the emulsion.

30. An oil-in-water emulsion according to claim 29, wherein said fatty phase is present in an amount ranging from 3% to 20% by weight with respect to the total weight of the emulsion.

31. An oil-in-water emulsion according to claim 1, wherein said aqueous phase is present in an amount ranging from 15% to 97.5% by weight with respect to the total weight of the emulsion.

32. An oil-in-water emulsion according to claim 31, wherein said aqueous phase is present in an amount ranging from 40% to 70% by weight with respect to the total weight of the emulsion.

* * * * *